United States Patent [19]

Horsfall, III et al.

[11] 3,963,576

[45] June 15, 1976

[54] METHOD FOR RENDERING BACTERIA DORMANT AND THE PRODUCT PRODUCED THEREBY

[75] Inventors: Frank L. Horsfall, III, Cleveland; Barton Gilbert, University Heights, both of Ohio

[73] Assignee: General Environmental Science Corporation, Cleveland, Ohio

[22] Filed: Feb. 21, 1975

[21] Appl. No.: 551,702

[52] U.S. Cl. .................................. 195/59; 195/96; 195/100; 195/112
[51] Int. Cl.² ............................................ C12K 1/00
[58] Field of Search ................ 195/96, 100, 59, 112

[56] References Cited
UNITED STATES PATENTS
3,880,740   4/1975   Mimura et al. ...................... 195/96

*Primary Examiner*—A. Louis Monacell
*Assistant Examiner*—Robert J. Warden
*Attorney, Agent, or Firm*—Fay & Sharpe

[57] ABSTRACT

A method for rendering bacteria dormant is provided which includes the steps of growing bacteria under aerobic conditions in an aqueous media in such a manner that the so-produced bacteria include at least one species of Pseudomonas bacteria which is capable of enzymatically reducing nitrate to nitrogen and one species of Rhodopseudomonas bacteria which is capable of photosynthetically forming red pigment; dissolving an effective amount of at least one compound selected from the group consisting of the sulfides of sodium and potassium in the bacteria containing media; and exposing the sulfide containing media under anaerobic conditions to light for a period of time sufficient to cause red photosynthetic pigment to develop in the Rhodopseudomonas bacteria. The product produced is a suspension of dormant bacteria.

20 Claims, No Drawings

METHOD FOR RENDERING BACTERIA DORMANT AND THE PRODUCT PRODUCED THEREBY

BACKGROUND OF THE INVENTION

Disposal of waste whether it be of human origin, from food preparation, from domestic animals, or from decaying plants and micro-organisms has, in the past, been treated as a natural process that can be accomplished effectively by those organisms present in the waste itself or those with which the waste will eventually come into contact during the natural treatment process. This approach sufficed in rural areas of low population density where small amounts of waste were exposed to decomposition. However, when high waste concentration and the use of man made facilities became the accepted mode of treatment in municipalities and on farms and waste consolidation in open toilets, lagoons or similar holding facilities became the norm in waste disposal, neither contact with soil organisms nor sufficient time for decomposition of the waste were available. The fecal organisms in human and animal waste had accomplished most of what they could in the intestine and were of little value in waste treatment facilities. All too soon it became apparent that holding facilities and treatment complexes were not functioning properly since noxious odors were present and incompletely decomposed waste was being discharged from the facilities.

Originally, most of the solutions offered to solve the problems of odor control, overloading of organic waste in existing facilities or treatment of special wastes were simply to expand existing facilities. Eventually, it was felt that a simpler and more effective method was to introduce bacteria of known functions into existing facilities to thereby enhance waste decomposition. Today many products are on the market which claim to aid or accelerate waste decomposition. Generally, these products are either enzymes, freeze-dried bacteria, fungi or various chemicals.

Of these techniques, the use of freeze-dried bacteria is especially appealing due to the fact that it minimizes the number of foreign substances which are to be added to the system being treated. However, it is well known that many bacteria die quickly if left dormant in dilute suspension or form spores that require time to germanate before becoming metabolically functional. For example, it is known that when freeze-dried bacteria are reactivated often as much as 95 percent, or higher, of the original bacteria die and are therefore of no significant assistance in breaking down or decomposing the waste products being treated. Therefore, a method of reactivating and sustaining bacterial viability in dilute suspension for long periods of time was sought. The instant invention provides such a technique, the advantages of which are obvious to those skilled in the art.

SUMMARY OF THE INVENTION

The present invention relates to a method for rendering bacteria dormant and the product produced thereby. More specifically, the instant invention concerns a method for rendering an aqueous suspension of bacteria dormant which method comprises (a) growing bacteria under aerobic conditions in an aqueous media in such a manner that the so-produced bacteria include at least one species of Pseudemonas bacteria which is capable of enzymatically reducing nitrate to nitrogen and one species of Rhodopseudomonas bacteria which is capable of photosynthetically forming red pigment, (b) dissolving an effective amount of at least one compound selected from the group consisting of the sulfides of sodium, potassium and mixtures thereof in the concerned bacteria containing media, and (c) exposing the sulfide containing media under anaerobic conditions to light for a period of time sufficient to cause red photosynthetic pigment to develop in the Rhodopseudomonas bacteria. The present invention also concerns the product which is obtained by the practice of the foregoing method.

The problems associated with the treatment of waste are myriad. For example, from a chemical standpoint, noxious odors in sewage treatment facilities result from the production of both ammonia gas and hydrogen sulfide gas, as well as the partial anaerobic digestion of protein waste. Once $NH_3$ (ammonia) has formed, the pH of the system begins to rise and organisms sensitive to high pH and the presence of $NH_3$, a metabolic poison, die. Then, once ammonia oxidation has depleted local oxygen supplied, organisms capable of sulfide production flourish, creating a real odor problem. One approach to solving the above problem is to slow down or eliminate the production of free ammonia. In this regard, there are two bacteria, nitrosomonas and nitrobacter, that cooperate to convert ammonia ($NH_3$) to nitrate ($NO_3$). Once formed, however, the nitrate will limit its own production. Additionally, acid is created during the process of ammonia oxidation. In a soil environment, green plants utilize the nitrate produced from the oxidation of ammonia. In an aqueous solution, plants and algae utilize the nitrate as a nitrogen source for growth. There are bacteria, denitrifying bacteria, that will convert $NO_3$ to nitrogen ($N_2$) gas, thereby removing the nitrate from the water or waste treatment facility. Therefore, if a cycle can be set up in which $NH_3$ can be converted to $N_2$ via nitrate, the pH of the system will increase instead of becoming acid through ammonia oxidation above, and a noxious compound, $NH_3$ will be converted to an innocuous one, $N_2$. Furthermore, the nitrate serves as an effective electron acceptor in the absence of oxygen and during the reduction of nitrate to nitrogen, substances like sulfur can be converted to sulfate, further aiding in the removal of odor-causing compounds.

The equations that describe these reactions are as follows:

Ammonia oxidation to nitrite:

$$2NH_3 + 3O_2 \rightarrow 2NO_2^- + 2H^+ \; 2H_2O$$

Nitrite oxidation to nitrate:

$$2NO_2^- + O_2 \rightarrow 2NO_3^-$$

Nitrate reduction to nitrogen:

$$2NO_3^- + 10 \text{ electrons } (e^-) + 12H^+ \rightarrow N_2 + 6H_2O$$

Nitrate reduction with sulfur oxidation:

$$5S + 6NO_3^- + 2H_2O \rightarrow 5SO_4 + 3N_2 + 4H^+$$

It is noted that sulfur oxidation proceeds without molecular oxygen. Such oxidations coupled to nitrate reduction are not limited to inorganic compounds. Acetate for example, can also be oxidized to carbon dioxide concommittantly with nitrate reduction. This equation gives the stoichiometry;

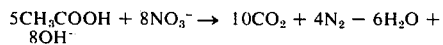

Again no molecular oxygen is consumed.

Prior art techniques for accomplishing the foregoing have all met with limited success. As before noted, those techniques which utilize bacteria which have been rendered dormant (for example by freeze drying) all suffer from the fact that most of the bacteria are killed in the inactivation process.

Accordingly, it is an object of the present invention to provide a method of rendering bacteria dormant without significantly effecting their ability to be subsequently reactivated.

Other objects of the invention will be apparent to those skilled in the art from a reading of the instant specification and claims.

DESCRIPTION OF THE PREFERRED EMBODIMENTS OF THE INVENTION

The preferred practice of the invention concerns a unique method for rendering bacteria dormant and the product so produced. Broadly stated, the method of the invention comprises the steps of (a) growing bacteria under aerobic conditions in an aqueous media in such a manner that the so-produced bacteria include at least one species of Pseudemonas bacteria which is capable of enzymatically reducing nitrate to nitrogen and one species of Rhodopseudomonas bacteria which is capable of photosynthetically forming red pigment, (b) dissolving an effective amount of at least one compound selected from the group consisting of the sulfides of sodium, potassium and mixtures thereof in the concerned bacteria containing media, and (c) exposing the sulfide containing media under anaerobic conditions to light for a period of time sufficient to cause red photosynthetic pigment to develop in the Rhodopseudomonas bacteria.

In the practice of the instant invention, live bacteria of several strains are grown in an aqueous suspension. In one specific example, the suspension is prepared by growing the bacteria together in a vat or kettle using the following ingredients (nutrients) that are sterilized prior to innoculation with the bacteria:

| Grams/Liter | Percent | |
|---|---|---|
| 1.0 gm/liter | (0.1%) | Ammonium Chloride (NH$_4$Cl) |
| 1.0 gm/liter | (0.1%) | Monobasic Potassium Phosphate (KH$_2$PO$_4$) |
| 0.5 gm/liter | (0.05%) | Magnesium Sulfate (MgSO$_4$.7H$_2$O) |
| 2.0 gm/liter | (0.2%) | Sodium Acetate (NaC$_2$H$_3$O$_2$.7H$_2$O) |
| 1.0 gm/liter | (0.1%) | Yeast Extract |

The above percentages, as are all others recited herein, are given as a weight of compound per volume of solution used to dissolve it. The above ingredients are dissolved in distilled or deionized water to which has been added ten percent tap water to provide trace elements. Sterilization is allowed to continue for one hour at 125°C.

Growth is initiated by introducing six species of bacteria, one Bacillus (gram positive spore forming rods), one Rhodopseudomonas (photosynthetic non sulfur purple gram negative non spore forming rods), and four Pseudomonas (gram negative non spore forming rods, at least one of which is capable of reducing nitrate to nitrogen or nitrous oxide gases). The bacteria are grown at 25° – 30°C. under vigorous aeration for 18 – 24 hours during which time their total concentration reaches 2–5 × 10$^6$ cells per milliliter.

After the aerobic growth is completed, a sample of the bacterial suspension is removed to provide a fresh innoculum for the next growth cycle. One hundred grams of sodium sulfide (Na$_2$S.9H$_2$O) is added to 100 liters of suspension (making the sodium sulfide concentration 1.0 grams/liter). This suspension is then placed in a plurality of translucent polyethylene containers which are kept in the light (fluorescent) for an additional 24 hours. During this time the red photosynthetic pigment develops in the Rhodopseudomonas. The bacteria were kept anaerobically for 24 hours during which time significant amounts of the Rhodopseudomonas bacteria had turned red. The so-produced and treated suspension was then placed in cartons and stored prior to use. No further precautions are necessary except to insure they do not freeze, nor reach a temperature in excess of about 50°C. for an extended period of time.

The foregoing example is simply illustrative of the practice of the described and claimed invention. Obviously, various departures may be made from the above-described procedure without deviating from the spirit and scope of the invention. For example, other systems may be utilized to grow the desired bacteria, and as these systems are well known to those skilled in the art they will not be discussed herein in detail.

Likewise the specific type of bacteria grown is not critical, except that it must contain at least one species of Pseudemonas bacteria which is capable of enzymatically reducing nitrate to nitrogen and one species of Rhodopseudomas bacteria which is capable of forming red pigment. (It is to be noted that while in the foregoing example four species of Pseudomonas are utilized, only one species thereof needs to be present to realize the benefits of the instant invention.

In addition, while it is preferred to grow the concerned bacteria under the stated conditions it is well within the ambit of the present invention to vary these parameters. For example, it is generally desired to grow the concerned bacteria at temperatures ranging from about 15° to about 35°C to an amount sufficient to produce a cell concentration of at least 1 × 10$^6$ cells per milliliter.

Sodium or potassium sulfides, or mixtures thereof, including but not limited to Na$_2$S, K$_2$S, NaHS and KHS, are equally effective in the practice of the instant invention. However, sodium sulfide is generally preferable due to the fact that it is the least expensive of these compounds. The exact amount of the sulfide compound to be utilized may vary depending on the attendant circumstances. In practice, all that is required is that an effective amount of sulfide compound be utilized. That is, enough sulfide compound must be employed to insure that the bacteria are rendered dormant but capable of being reactivated without destroying a significant percentage thereof. Generally, however, it is preferred to utilize a given sulfide compound in a concentration, based on the sulfide (sulfur) content of the compound ranging from about 0.07 to about 0.3 grams/liter. Obviously, the exact amount of sulfide material to be utilized will vary depending on the specific compound employed. For example, in the case of Na$_2$S.9H$_2$O it is preferred to utilize it in an amount ranging from about 0.5 to about 2.0 grams of $Na_2S \cdot 9H_2O$ per liter of suspension.

The so-treated bacteria are exposed to light for a period of time sufficient to cause red photosynthetic pigment to develop in the Rhodopseudomonas bacteria. Obviously, the duration of such exposure may vary depending on the attendant circumstances, such as growth temperature and specific types of bacteria grown.

In the practice of the instant invention, the sulfide serves to lower the electrochemical potential sufficiently to induce the development of the photosynthetic pigment. It also provides an environment that allows the pseudomonads which are capable of reducing nitrate to nitrogen or nitrous oxide gases to survive for an indefinite period of time. These pseudomonads will die out with a half life of one month in suspensions to which sulfide has not been added. The Rhodopseudomonas die out with a longer half life, while the Bacillus do not seem to die out at all but do produce spores in suspensions that do not contain sulfide.

All the reactions that bacteria treated according to the present invention can perform cannot be discussed, for many of them are unknown. It is quite possible that our understanding of how the odor of ammonia and hydrogen sulfide is removed is incomplete. Functionally, however, it is apparent that the control of odor and many other organic reactions are taking place as a direct result of the presence of bacteria which has been rendered dormant by the technique described herein and subsequently reactivated in use.

It is to be noted that a 3.8 liter sample of bacteria produced as before described has been stored for a period of time of about 12 months and then tested for efficacy with the result being that in excess of 90 percent of the original bacteria were still viable when reactivated. This result contrasts with a viability percentage of about 0.1 for similar bacteria which were not treated in accord with the technique of the instant invention.

Bacteria produced as described herein have been and can be used in the following instances:
1. Pit and Cement Vault Toilets;
2. Sewage Treatment Plants of all varieties;
3. Septic Systems and Drainage Fields for home, farms and multiple dwellings;
4. Grease Traps;
5. Ponds and Lagoons, both sewage and recreational;
6. Aquariums, both private and commercial;
7. Dog waste repository systems;
8. Waste holding tanks in airplanes, campers, recreational vehicles and boats;
9. Drain lines and down pipes in all types of buildings.

In systems where human waste is either contained or treated, the usual odor of ammonia or hydrogen sulfide is not present if those systems are treated with material produced according to the instant invention. In addition, during waste treatment, nitrate does not accumulate and organic solid waste is reduced substantially (30–50%) from similar situations not using the material of the instant invention. During anaerobic digestion of solids and sludge from the activated sludge or primary aeration tank types of sewage treatment, more gas with a higher percentage of methane than carbon dioxide is produced if the material of the invention is added to the anaerobic digester. Finally, total Biochemical Oxygen Demand (BOD) in the effluent from sewage treatment plants is reduced in facilities using the material of the instant invention compared to similar facilities not using the same.

In situations where the type of waste is not excretory in nature, but is material like fat, lipid, grease and blood such as from restaurants or slaughter houses, this waste is effectively decomposed by the material of the instant invention. Decomposition will occur in the pipes as well as in the grease traps and holding tanks used by these facilities.

Within ponds or lagoons located in recreational facilities or on farms, the types of activity observed by adding the material of the instant invention to them are similar to those described for pit toilets and sewage treatment plants. Since bacteria treated according to the instant invention are capable of growth on waste and of metabolizing that waste, it is possible to treat one million times the volume of added material. In fact, this dosage is the recommended one, more being used in unusual circumstances or when results are desired quickly.

By adding the material of the instant invention to an aquarium, one can decrease the amount of solid waste accumulating on the bottom of the tank, increase the time between filter changes, improve the clarity of the water by limiting algal growth, provide a more diverse bacterial population in the tank which is healthy and finally, provide food material for protozoa and other invertebrates on which the fish feed.

In holding facilities stronger dosages of the material of the invention are required, since results are desired quickly. Principally, the objective is to prevent the onset of odors during flight or between use and emptying of the holding tank. This is an unusual situation in that previous uses of the product of the invention involve an open ended treatment cycle. However, tests to date clearly indicate that the material of the instant invention is effective for this purpose.

While there have been described herein what are, at present, considered to be the preferred embodiments of the invention, it will be obvious to those skilled in the art that various changes and modifications may be made therein without departing from the spirit and scope of the invention as hereinafter claimed.

What is claimed is:

1. A method for rendering an aqueous suspension of bacteria dormant which comprises,
    a. growing bacteria under aerobic conditions in an aqueous media in such a manner that said bacteria includes at least one species of Pseudemonas bacteria which is capable of enzymatically reducing nitrate to nitrogen and one species of Rhodopseudomonas bacteria which is capable of photosynthetically forming red pigment;
    b. dissolving an effective amount of at least one sulfide compound selected from the group consisting of the sulfides of sodium, potassium and mixtures thereof in said bacteria containing media; and
    c. exposing said sulfide containing media under anaerobic conditions to light for a period of time sufficient to cause red photosynthetic pigment to develop in the Rhodopseudomonas bacteria.

2. The method of claim 1 wherein the concentration of sulfide compound, based on the sulfide (sulfur) content of said compound, ranges from about 0.07 to about 0.3 grams per liter.

3. The method of claim 2 wherein said sulfide compound is sodium sulfide.

4. The method of claim 3 wherein said bacteria are grown using a nutrient system comprising:
   a. ammonium chloride,
   b. monobasic potassium phosphate;
   c. magnesium sulfate;
   d. sodium acetate, and
   e. yeast extract.

5. The method of claim 4 wherein the bacteria grown further includes Bacillus and Pseudomonas bacteria.

6. The method of claim 1 wherein the concentration of cells grown in step (a) is at least $1 \times 10^6$ cells per milliliter of solution.

7. The method of claim 5 wherein said bacteria are grown at a temperature ranging from about 25° to about 30°C for a period of about 18 to 24 hours, whereby the total cell concentration of bacteria ranges from about 2 to about 5 million cells per milliliter of solution.

8. The method of claim 7 wherein the amount of sodium sulfide is about 1.0 grams per liter.

9. The method of claim 1 wherein step (c) is continued for a period of time sufficient to cause the Rhodopseudomonas to develop photosynthetic red pigment.

10. The method of claim 9 wherein step (c) is continued for a period of about 24 hours.

11. An aqueous suspension of dormant bacteria obtained by:
    a. growing bacteria under aerobic conditions in an aqueous media in such a manner that said bacteria includes at least one species of Pseudemonas bacteria which is capable of enzymatically reducing nitrate to nitrogen and one species of Rhodopseudomonas bacteria which is capable of photosynthetically forming red pigment;
    b. dissolving an effective amount of at least one sulfide compound selected from the group consisting of the sulfides of sodium, potassium and mixtures thereof in said bacteria containing media; and
    c. exposing said sulfide containing media under anaerobic conditions to light for a period of time sufficient to cause red photosynthetic pigment to develop in the Rhodopseudomonas bacteria.

12. The aqueous suspension of claim 11 wherein the concentration of sulfide compound, based on the sulfide (sulfur) content of said compound, ranges from about 0.07 to about 0.3 grams per liter.

13. The aqueous suspension of claim 12 wherein said sulfide compound is sodium sulfide.

14. The aqueous suspension of claim 13 wherein said bacteria are grown using a nutrient system comprising:
    a. ammonium chloride,
    b. monobasic potassium phosphate;
    c. magnesium sulfate;
    d. sodium acetate, and
    e. yeast extract.

15. The aqueous suspension of claim 14 wherein the bacteria grown further includes Bacillus and Pseudomonas bacteria.

16. The aqueous suspension of claim 11 wherein the concentration of cells grown in step (a) is at least $1 \times 10^6$ cells per milliliter of solution.

17. The aqueous suspension of claim 15 wherein said bacteria are grown at a temperature ranging from about 25° to about 30°C. for a period of about 18 to 24 hours, whereby the total cell concentration of bacteria ranges from about 2 to about 5 million cells per milliliter of solution.

18. The aqueous suspension of claim 17 wherein the amount of sodium sulfide is about 1.0 grams per liter.

19. The aqueous suspension of claim 11 wherein step (c) is continued for a period of time sufficient to cause the Rhodopseudomonas to develop photosynthetic red pigment.

20. The aqueous suspension of claim 19 wherein step (c) is continued for a period of about 24 hours.

* * * * *